United States Patent [19]

Simpson

[11] Patent Number: 4,740,695

[45] Date of Patent: Apr. 26, 1988

[54] IONIZATION DETECTORS FOR GAS CHROMATOGRAPHY

[75] Inventor: Colin F. Simpson, Sussex, England

[73] Assignee: The Perkin-Elmer Corporation, Norwalk, Conn.

[21] Appl. No.: 787,563

[22] Filed: Oct. 15, 1985

[30] Foreign Application Priority Data

Dec. 14, 1984 [GB] United Kingdom ................ 8431663

[51] Int. Cl.[4] .......................................... B01D 59/44
[52] U.S. Cl. .................................. 250/282; 250/288; 250/423 P
[58] Field of Search ................... 250/282, 288, 423 R, 250/423 P, 427; 315/111.81; 73/23.1

[56] References Cited

U.S. PATENT DOCUMENTS

| 2,950,381 | 8/1960 | Brubaker | 250/423 P |
| 3,959,677 | 11/1960 | Robinson et al. | 250/423 P |
| 4,028,617 | 6/1977 | Kamo et al. | 250/423 P |
| 4,368,388 | 1/1983 | Blyth | 250/288 |
| 4,377,749 | 3/1983 | Young | 250/423 P |
| 4,413,185 | 11/1983 | Leveson et al. | 250/423 P |
| 4,476,392 | 10/1984 | Young | 250/423 P |

Primary Examiner—Bruce C. Anderson
Attorney, Agent, or Firm—Francis L. Masselle; Ronald G. Cummings; Edwin T. Grimes

[57] ABSTRACT

There are disclosed gas chromatographic ionization detectors of the argon and electron capture types. The free electrons required for the functioning of the detectors is achieved by irradiating a solid photoemissive element with ultraviolet radiation.

7 Claims, 3 Drawing Sheets

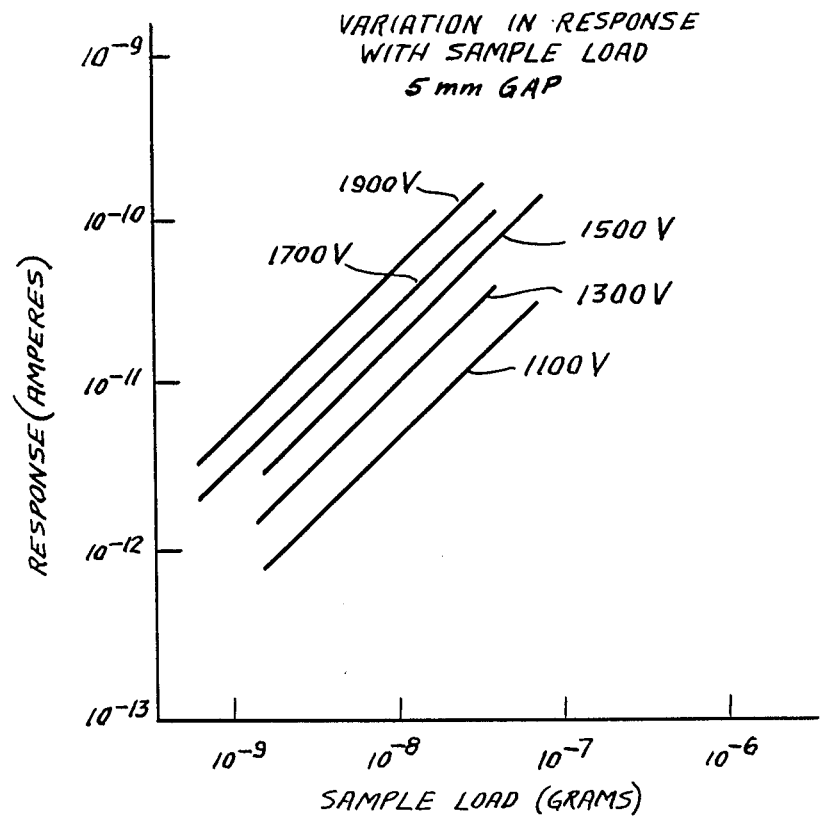
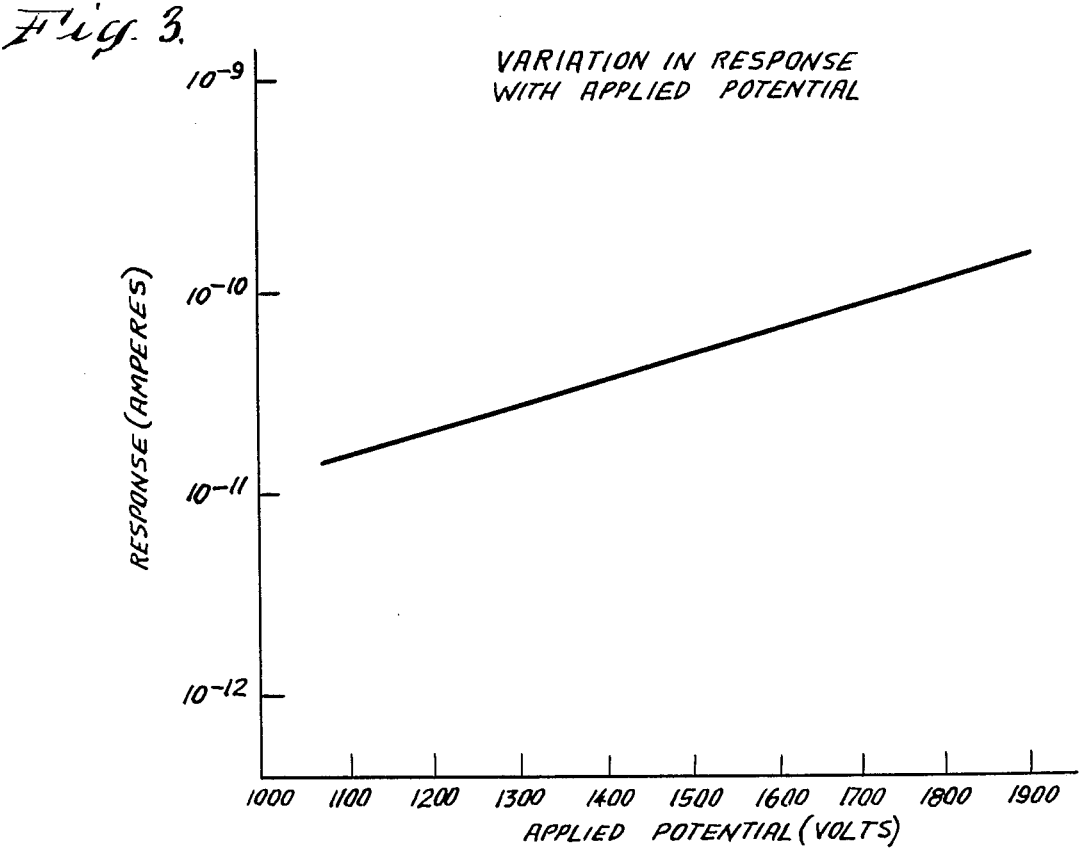

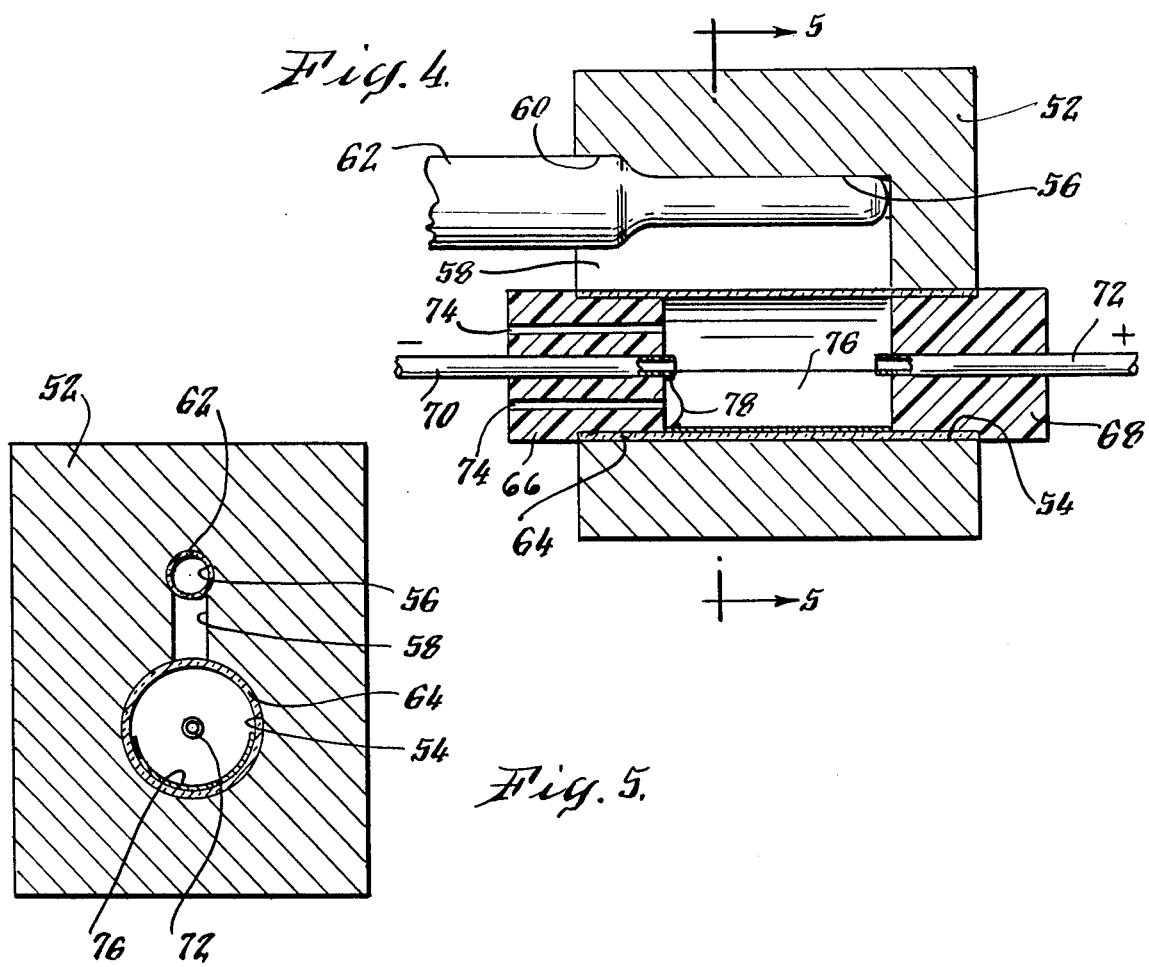
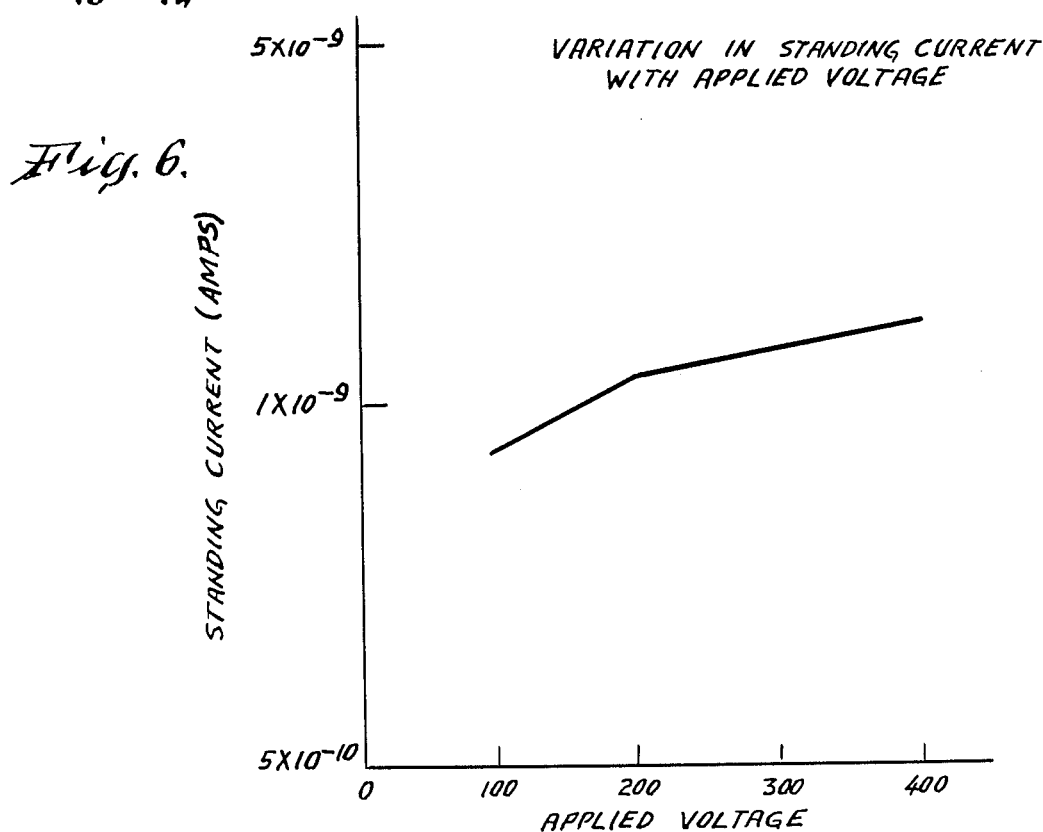

IONIZATION DETECTORS FOR GAS CHROMATOGRAPHY

TECHNICAL FIELD

This invention pertains to gas chromotography detectors, more particularly, to such detectors of the ionization type.

BACKGROUND ART

Ionization detectors for gas chromatography are well known in the art. A comprehensive survey of such detectors as of 1961 may be found in an article entitled "Ionization Methods for the Analysis of Gases and Vapors" by J. E. Lovelock, *Analytical Chemistry*, Volume 33, No. 2, February 1961, pages 162–178. The detectors reviewed in that article include, inter alia, the cross-section ionization detector, the argon detector, and the electron capture detector. These detectors are characterized by the fact that each includes a source of ionizing radiation, i.e., a radioactive material.

The use of radioactive substances in chromatographic detectors necessarily introduces certain health risks into the laboratory and complicates such tasks as cleaning detectors after use. Because of these health risks, they are also subject to certain governmental controls which complicate their application and use.

Ionization detectors have been developed which avoid the need for radioactive elements. However, in many cases, these are not suitable for use as argon and electron capture detectors for various reasons, including the fact that they may require gases other than the carrier or sample. Examples are the photo-ionization detector referenced in the above-mentioned Lovelock article and the flame ionization detector.

More recently, an electron capture detector has been developed which utilizes a thermionic emission electron source. Such a detector is described in U.S. Pat. No. 4,304,997 of Sullivan et al. However, there are certain problems inherent in a thermionic detector. One such problem is that the emitting filament may be "poisoned" by components of many samples—i.e., components may be adsorbed on the surface and thereby reduce its thermal emission.

For the foregoing reasons, it would be desirable to provide an ionization detector which would avoid the use of ionizing radiation, additional gases, and heated filaments.

DISCLOSURE OF THE INVENTION

The present invention is a detector for use in gas chromatography of the type which includes a detection chamber, an electrical potential established across the chamber, and means for supplying free electrons to the chamber. The electrons are supplied by positioning a solid photoemissive element adjacent the chamber and irradiating the photoemissive element with ultraviolet radiation.

BRIEF DESCRIPTION OF DRAWINGS

FIG. 2 is a graph illustrating the response of the detector of FIG. 1 with sample loads;

FIG. 3 is a graph illustrating the variation in the response of the detector of FIG. 1 with applied potential;

FIG. 4 is a cross-section of an electron capture detector in accordance with the present invention;

FIG. 5 is a cross-section taken substantially along the line 5—5 of FIG. 4; and

FIG. 6 is a graph showing the variation in standing current with applied voltage of the detector of FIGS. 4 and 5.

BEST MODE FOR CARRYING OUT THE INVENTION

Figure 1:
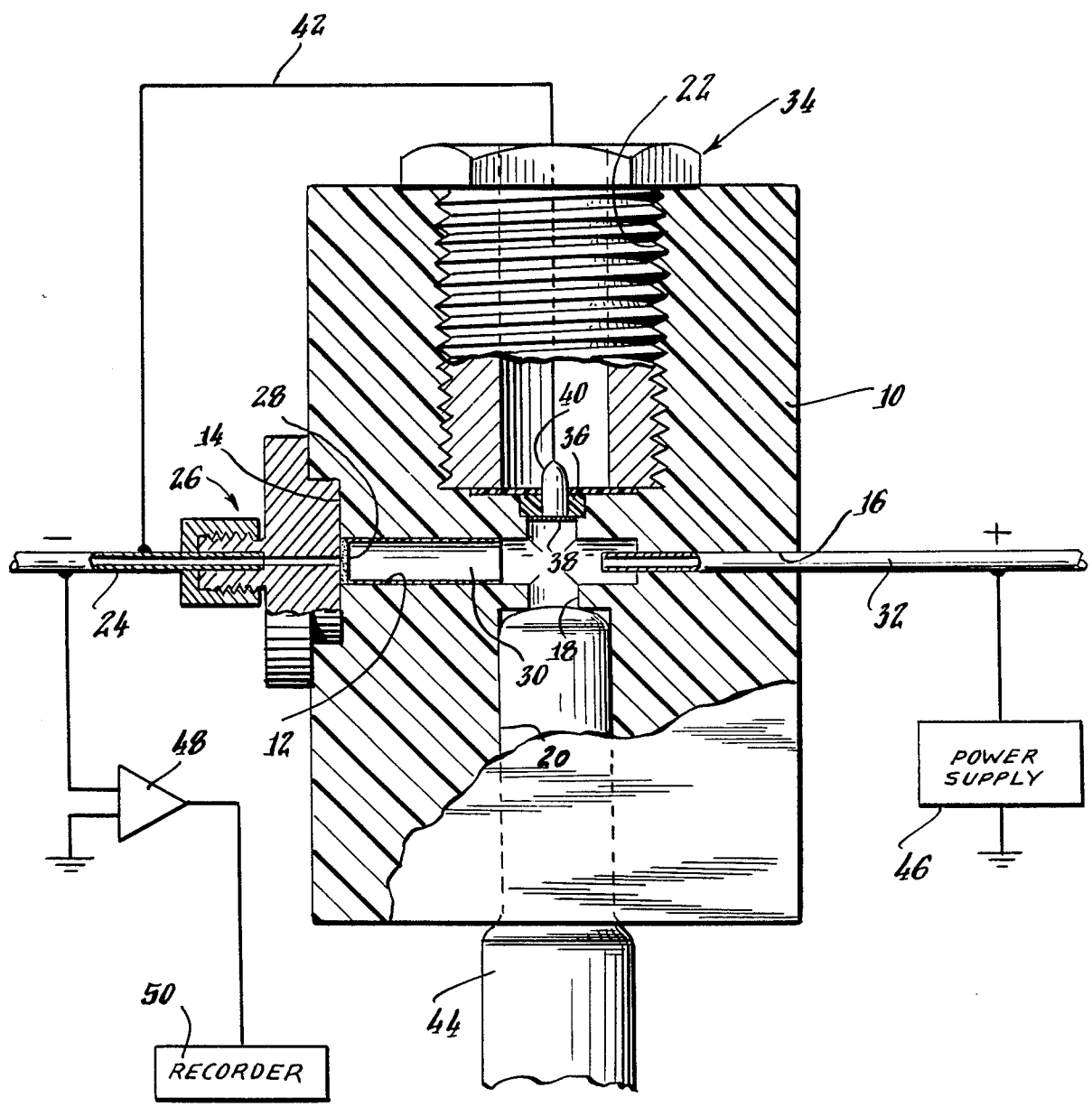
FIG. 1 is an illustration, in partial cross-section, of an argon detector in accordance with the present invention.

In accordance with the present invention, there is provided an ionization detector for gas chromatography which does not require a radioactive source. Instead, the electron source is a solid state photoemitter irradiated with ultraviolet light. More specifically, one such detector is of the type wherein the electrons raise argon to its metastable state. In another such detector, electrons are captured by sample components to form an electron capture detector.

With particular reference to FIG. 1, there is disclosed an argon detector in accordance with the present invention. The body 10 of the detector is a block of a substantially inert, non-metallic material, in this instance, polytetrafluoroethylene (PTFE). The block is drilled to provide a substantially horizontal passage 12 extending from a recess 14 in the left side of body 10 as viewed in FIG. 1. The passage 12 is coaxial with a smaller passage 16 which continues out the righthand side of the body 10. The passage 12 is intersected by a vertical passage 18 which communicates with a well 20 extending out the bottom of body 10 and a larger tapped opening 22 which extends out the top of body 10. The end of a chromotographic column 24 is connected into the passage 12 by means of a conventional stainless steel, liquid chromotograph column end fitting 26 carrying a two micron frit disc 28. The fitting is press fitted into the recess 14 and is in electrical connection with a tubular, copper foil electrode 30 lining the passage 12. The electrode 30, fitting 26, and column 24 comprise the cathode of the detector. The anode comprises a stainless steel tube 32 inserted into the passage 16. In one embodiment the tube 32 had an outer diameter of 1/16 inch and an inner diameter of 0.020 inch.

Screwed into the tapped opening 22 is a threaded plug 34 which is hollow and carries at its end a holder 36 to which is secured, as by cementing, a small piece of photoemissive foil 38. This foil may be any material which is activated by ultraviolet radiation. In one embodiment, approximately three square millimeters of an antimomy cesium (Sb/Cs) alloy foil emitter from an EMI 9781R photoemitter was employed. Other stable photoemitters could also be employed including, for example, the multi-alkali (Na-K-Sb-Cs) photocathode from a Hamamatsu R955 photomultiplier tube. This material has a high radiation sensitivity between 930 nm and 160 nm. The foil 38 was electrically connected to the cathode by means of a suitable connector 40 and condutor 42. The ultraviolet source for the detector was a Hamamatsu "pencil" ultraviolet lamp 44 inserted into the well 20.

Ultraviolet radiation from the lamp 44 bombards the photoemissive foil 38, resulting in a cloud of electrons in the detection chamber formed by passage 12. When argon (or a similarly acting gas such as helium) is used as the carrier to elute samples from the chromatographic column 24, the argon atoms are raised to their metastable state by electron collisions and then the metastable argon atoms ionize the sample molecules as explained by Lovelock. This causes a current flow across the applied potential between anode 32 and cathode 30 produced by the power supply 46. This current flow is amplified by amplifier 48 and recorded by recorder 50.

The spatial position of the anode 32 with respect to the cathode 30 determines the level of response at a given applied potential. The response increases with applied potential at a given electrode separation, as illustrated in FIG. 3. A good general working condition is a five millimeter electrode gap and fifteen hundred volts applied potential. For more sensitive modes of operation, an increase of applied potential to two thousand volts provides an order of magnitude increase in response, as shown by the graph of FIG. 2.

Another factor affecting operation of the detector is the area of emitter foil which is exposed. Obviously, the electron flux is proportional to the surface area of the emitter exposed to the ultraviolet light and also to the intensity of the radiation. Furthermore, it is important that the anode 32 should present a smooth, polished, rounded surface. This avoids arcing at high voltages. Various modifications will also be obvious to those skilled in the art. These might include, for example, a stainless steel construction utilizing a minimum of plastic in order to electrically isolate the anode. Also, the ultraviolet radiation might be introduced via a quartz light pipe and noise reduction might be achieved by introduction of a third electrode to collect the ions produced, as in Lovelock's triode detector.

A further modification of this invention is illustrated in FIGS. 4 and 5. In this modification, the use of photoemission as an electron source is employed in an electron capture detector. As is well known to those skilled in the art, in an electron capture detector, an ion chamber which contains a cloud of free electrons is maintained at a potential just sufficient for the collection of all the free electrons produced. When there is introduced into such an ion chamber, a gas or vapor capable of capturing free electrons, a corresponding decrease in current flow is readily observable. This is a very sensitive detector for certain specific components, in particular, oxygen and halogenated compounds. Nitrogen is the most commonly used carrier gas.

The electron capture detector illustrated in FIGS. 4 and 5 comprise a metallic body 52 which may be, for example, of stainless steel or aluminum. It has a horizontal cylindrical bore 54 therethrough and a parallel, cylindrical recess 56 extending substantially therethrough. The bore 54 and the recess 56 are joined by a vertical slot 58. The left end of the recess 56, as viewed in FIG. 4, is provided with a flare 60 so as to receive and conform to the shape of an ultraviolet lamp 62. The inner surfaces of recess 56, slot 58, and bore 54 are highly polished to enhance the reflection of ultraviolet radiation.

A quartz tube 64 is mounted within the bore 54. This tube in one embodiment was 45 millimeters long and had an internal diameter of 14 millimeters. The ends of the tube are terminated by PTFE plugs 66, 68. The plugs 66, 68 have identical coaxial openings therethrough for receiving respective cathode 70 and anode 72, each of which is formed from a stainless steel tube of 1/16" OD and 1/32" ID. In addition, the plug 66 is provided with scavenging holes 74. Mounted within and against the lower inner circumference of the quartz tube 64 is a piece of photoemissive foil 76 electrically connected to the cathode 70 by means of a lead 78. In an actual embodiment, the foil 76 was 15×25 millimeters in size.

The ultraviolet lamp 62 was a Hamamatsu ultraviolet lamp and, as will be apparent from the drawing, particularly FIG. 5, its radiation was caused to pass directly through the slot 58 and the quartz tube 64 onto the surface of the photoemissive foil 76. The standing current thereby achieved at various applied voltages is shown in the graph of FIG. 6.

A detector constructed in accordance with the foregoing description was set up with a nitrogen flow of 50 millimeters per minute passing in through the tubular cathode 70. This detector responded well to samples of dichloroethane, chloroform, and trichloroethylene. However, hexane and heptane resulted in substantially no response. This clearly illustrated that the detector operated in the electron capture mode, as only halogenated compounds gave suitable responses.

It will be apparent to those skilled in the art that a number of variations may be made in the design and construction of this modification of electron detector cell. For example, the ultraviolet lamp could be totally contained within the detector body so that ultrviolet energy may radiate over a cylinder the length of the emitter. Alternatively, ultraviolet energy could be passed into a cell through a light pipe having a hemispherical end to ensure even distribution of radiation. These techniques would enable construction of a smaller cell which could be more readily scavenged. Another modification would employ the ultraviolet lamp as an anode by covering it with a fine metal mesh. Furthermore, scavenging gas may be admitted into the detector cell, ideally as an annular flow close to the walls of the detector-cell, while the sample enters the cell axially. This would help protect the emitter from contamination.

It will also be apparent that a number of other variations and modifications may be made in this invention without departing from its spirit and scope. Accordingly, the foregoing description is to be construed as illustrative only, rather than limiting. This invention is limited only by the scope of the following claims.

What is claimed is:

1. In an apparatus for analyzing an unknown substance in a gaseous or vapor phase, a sample of which is entrained in a rare gas carrier, a detector comprising:
   a single chamber with associated flow passages for influx and outlet of the gas and entrained sample;
   a solid photoemissive element disposed in said chamber responsive to photoirradiation to emit electrons for raising atoms of the rare gas carrier to a metastable state, collison of said metastable atoms with molecules of said sample effecting ionization of said molecules;
   means for directing photons onto said photoemissive element to cause emission of electrons;
   means for impressing an electrical potential across said chamber; and
   means responsive to electric current flowing through said chamber due to said potential for indicating the concentration of ionized sample molecules in said chamber.

2. Apparatus according to claim 1 wherein said photoemissive element is an alloy comprising antimony and cesium.

3. Apparatus according to claim 2 wherein said alloy includes sodium and potassium.

4. The method of analyzing the effluent from a fractionating column for the presence of sample gases or vapors entrained in a rare gas carrier which comprises:
- passing said effluent through an ionization region in the presence of a solid state photoemitter;
- irradiating said photoemitter with photons to emit electrons for raising the rare gas atoms to their metastable states;
- allowing the metastable rare gas atoms to collide with molecules of sample gas to ionize the sample gas molecules; and
- measuring the concentration of ionized sample gas molecules in said ionization region.

5. The method of claim 4 wherein said rare gas is argon.

6. The method of claim 4 wherein said concentration measurement comprises a measurement of current flow between electrodes at a selected potential difference.

7. The method of claim 6 wherein said photons are in the ultraviolet region.

* * * * *